United States Patent [19]
Heggie et al.

[11] Patent Number: 6,013,778
[45] Date of Patent: Jan. 11, 2000

[54] PROCESS FOR THE PREPARATION OF AZITHROMYCIN

[75] Inventors: William Heggie, Palmela; Zita Maria De Mouro Vaz Azevedo Mendes, Lisbon, both of Portugal

[73] Assignee: Hovione Inter Ltd., Switzerland

[21] Appl. No.: 09/080,856

[22] Filed: May 18, 1998

[30] Foreign Application Priority Data

May 19, 1997 [PT] Portugal .................................. 102006

[51] Int. Cl.⁷ .................................................... C07H 17/08
[52] U.S. Cl. .............................. 536/7.4; 536/7.1; 536/7.2; 514/29
[58] Field of Search ........................... 536/7.1, 7.2, 17.2, 536/17.3, 7.4, 17.9, 18.5, 125; 514/29

[56] References Cited

U.S. PATENT DOCUMENTS

| | | |
|---|---|---|
| 4,474,768 | 10/1984 | Bright . |
| 4,517,359 | 5/1985 | Kobrehel et al. . |
| 5,686,587 | 11/1997 | Yang . |

FOREIGN PATENT DOCUMENTS

| | | |
|---|---|---|
| 0109253 | 11/1983 | European Pat. Off. . |
| WO94/26758 | 11/1994 | WIPO . |

OTHER PUBLICATIONS

Paper E/257/87; Erythromycin Series, Part 13, Synthesis and Structure Elucidation of 10–Dihydro–10–deoxy–11–methyl–11–azaerythromycin; Slobodan Djokie, et al.; 1239–1261.

"Erythromycin Series, Part 11, Ring Expansion of Erythromycin A Oxime by the Beckmann Rearrangement"; J. Chem Soc. Perkin Trans. 1 1986; Slobodan Djokie, et al.; 1881–1890.

*Primary Examiner*—James O. Wilson
*Attorney, Agent, or Firm*—Ostrolenk, Faber, Gerb & Soffen, LLP

[57] ABSTRACT

The present invention describes a new process for the preparation of azithromycin from a suitable imino ether as precursor, characterised by the fact that the reduction and the reductive methylation of said imino ether are sequentially carried out with a noble metal catalyst and hydrogen in the presence of formaldehyde, or a source thereof, wherein both reactions can be conducted in the same reaction vessel.

9 Claims, No Drawings

PROCESS FOR THE PREPARATION OF AZITHROMYCIN

BACKGROUND OF THE INVENTION

Azithromycin is a well-known semi-synthethic macrolide antibiotic (U.S. Pat. Nos. 4,474,768 and 4,517,358), which is prepared through the expansion/inclusion of a nitrogen atom in the macrolide ring of erythromycin A, followed by reductive methylation. In this way, an antibiotic more stable and more effective than erythromycin A is obtained, particularly against gram-negative bacteria.

The reaction sequence to transform erythromycin A into azithromycin involves extremely strong and aggressive reaction conditions (compare, J. Chem. Soc. Perkin Trans. I, 1881 (1986)), and requires the isolation of intermediates, which, in certain conditions, are even more unstable than the starting material. Reaction conditions and isolation procedures must be at the same time both mild and have their parameters strictly controlled. This can result in additional problems when a laboratory scale process is put into practice at an industrial level. Under these circumstances, additional restrictions on the manufacturing process have to be implemented in order to ensure that azithromycin is obtained in good yield and high purity.

The transformation of erythromycin A into azithromycin involves: conversion of erythromycin into its oxime; Beckmann rearrangement of the oxime to produce the imino ether of erythromycin A; reduction of the imino ether to 9-deoxo-9a-aza-9a-homoerythromycin, and, finally, reductive N-methylation to obtain the final product.

The reduction of the imino ether and reductive methylation have so far been described as a two-step process (PCT Patent Application No. 94/02547-Publication No. 94/26758; European Patent No. 0 109 253), presumably because in these procedures, purification of the 9-deoxo-9a-aza-9a-homoerythromycin is required before proceeding to the next step.

According to the present invention, it has been found that a suitable imino ether of erythromycin can be reduced, and the product thus obtained can be subsequently submitted to reductive methylation in the presence of the same noble metal catalyst and in the presence of formaldehyde or a source thereof, without any isolation of the intermediate product. The two reactions already known per se can subsequently be conducted using the same catalytic system in the same reaction vessel and in the same reaction medium. By carefully choosing the reaction conditions, one can obtain a product of good purity and with a good yield. Thus, the present process represents a considerable industrial advantage over the prior art by reducing the number of reactors and manipulations, like the isolation of the intermediate product. The preferred reaction conditions are described hereinafter.

According to the previously published literature, the conditions which have been found to be most effective to carry out the reduction of the imino ether are: utilisation of reducing agents in stoichiometric amounts or high pressure hydrogenation using platinum (PCT Patent Application No. 94/02547-Publication No. 94/26758).

This is then followed by isolating cyclic amine, which is then subject to reductive methylation, employing the well-known Eschweiler-Clarke conditions—formaldehyde and formic acid in chloroform—or by hydrogenation—formaldehyde and hydrogen in the presence of a noble metal catalyst (U.S. Pat. No. 4,517,359, J. Chem. Res., 1988, 1239–1261).

The reduction by sodium borohydride (EU Patent No. 0109253, J. Chem Soc. Perkin Trans., I, 1986, 1881) involves an extremely exacting procedure as far as completion of the reaction and recovery of the product are concerned. The initial intermediate present in the reaction medium is apparently a boron containing complex, which must be destroyed in order that the 9-deoxo-9-a-aza-9a-homoerythromycin can be isolated. The complex in question must be eliminated under acid conditions and since, as is known, the macrolide in question is sensitive to acid media, the conditions for this step must be rigorously controlled.

This procedure becomes more problematic at the industrial scale, since the times of contact between the sensitive intermediate and the undesired aqueous acid medium are inevitably more prolonged.

DESCRIPTION OF THE INVENTION

In the present invention these difficulties are overcome by synthesizing the 9-deoxo-9a-aza-9a-homoerythromycin intermediate under mild conditions, which need not be isolated or purified prior to the following step. Naturally, isolation of this intermediate can be effected if so desired. The reduction is carried out at a temperature between 0–50° C., and the preferred range being between 20–25° C. At this temperature, side reactions such as hydrolysis of the glycosides present in the molecule are reduced, especially the hydrolysis involving the cladinose unit.

The preferred solvent is acetic acid containing different percentages of water. Organic solvents, such as ethanol, tetrahydrofuran, dioxane or mixtures thereof with water can also be used.

Pressures which lead to the best results and to acceptable reaction times are those between 20–70 bar, but other pressures outside these limits can also be used.

The preferred catalyst is 5% rhodium-on-carbon, although other noble metal catalysts, such as platinum, palladium or ruthenium, can also be used. The amount of rhodium used can vary from between 0.5 and 2% calculated with respect to the starting material, although other percentages outside this range can be used. However, the reaction times as a result of this are less suitable.

The suitable sources of formaldehyde are a 37% aqueous solution or paraformaldehyde, although other sources can be used. The amount of formaldehyde used can vary between 23 and 100 moles/mole of the imino ether. A smaller amount of catalyst may be further added so as to complete the reaction within a reasonable time.

If so desired, the catalyst can be recycled and re-used several times, thus rendering the process more economic.

The azithromycin is isolated by adjusting the pH of the reaction mixture between 9 and 10. In this manner, it is possible to obtain azithromycin of acceptable purity by crystallization from a mixture of ethanol/water, hence yielding a product with a sufficiently high purity to be used as starting material in the pharmaceutical industry.

Therefore, the present invention affords, among others, the following advantages:

2 chemical reactions in only one reaction vessel;

use of less sophisticated industrial equipment, given the fact that one of the intermediates is not isolated;

milder reaction conditions, giving a pure product with a high yield.

The following examples serve to illustrate the present invention and are not, in any way, to be considered a limitation thereof.

EXAMPLE 1

To a solution of 2 g (2.7 mmoles) of the imino ether of erythromycin A, prepared by the usual techniques, in 20 ml of acetic acid, there were added 0.03 g (0.38 mmoles) of sodium acetate and 0.5 g of wet 5% Rh/C (11.25 mg Rh). The mixture was then hydrogenated at a pressure of 70 bar and at 40° C. for 3 hours. At the end of this period, 27 ml of an aqueous solution containing 37% formaldehyde (0.36 moles) were added under atmospheric pressure and at room temperature, and the mixture hydrogenated at 40 bar and at a temperature of 40° C. for 20 hours. The catalyst was filtered off and the filtrate evaporated until an oil was obtained. To the oil so obtained, 45 ml of water were added, and the pH of the solution was adjusted to 9.3 with 4N NaOH. After stirring for 2 hours at room temperature, the solid was filtered, washed with water, and dried, yielding 1.2 g of crude azithromycin with a purity of 97% after recrystallization.

EXAMPLE 2

To a solution of 4 g (5.4 mmoles) of the imino ether of erythromycin A, prepared by the usual techniques, dissolved in 20 ml of acetic acid, 1 g wet 5% Rh/C (22.5 mg Rh) was added. The mixture was hydrogenated at 60 bar and at a temperature of 40° C. for 5 hours. At the end of this period, 22.5 ml of an aqueous solution containing 37% formaldehyde (0.3 moles) were added under atmospheric pressure and at room temperature, and the mixture was then hydrogenated at 40 bar and at a temperature of 40° C. for 20 hours. The catalyst was filtered off and the filtrate evaporated until an oil was obtained. To this oil, 90 ml of water were added, and the pH of the solution was adjusted to 9.4 with 4N NaOH. After stirring for 2 hours at room temperature, the solid was filtered, washed with water, and dried, yielding 2 g of crude azithromycin with a purity of 97% after recrystallization.

EXAMPLE 3

To a solution of 8 g (10.9 mmoles) of the imino ether of erythromycin A, prepared by the usual techniques, in 32 ml of acetic acid and 8 ml of water, there were added 8 g of wet 5% Rh/C (180 mg Rh). The mixture was then hydrogenated at 70 bar and at room temperature for 2 hours. At the end of this period, 40 ml of an aqueous solution containing 37% formaldehyde (0.54 moles) were added, and the mixture was hydrogenated at 40 bar and at a temperature of 40–45° C. for 20 hours. The catalyst was filtered off, and the pH of the filtrate was adjusted to 9.4 with 4N NaOH. After stirring for 2 hours at room temperature, the solid was filtered, washed with water, and dried, yielding 7 g of crude azithromycin with a purity of 95% after recrystallization.

EXAMPLE 4

To a solution of 4 g (5.4 mmoles) of the imino ether of erythromycin A, prepared by the usual techniques, in 4 ml of acetic acid and 16 ml of water, were added 4 g of wet 5% Rh/C (90 mg Rh). The mixture was hydrogenated at 70 bar and room temperature for 2 hours. At the end of this period, 25 ml of an aqueous solution containing 37% formaldehyde (0.34 moles) was added under atmospheric pressure at room temperature and the mixture was hydrogenated at 40 bar and at a temperature of 40–45° C. for 24 hours. The catalyst was filtered off, and the pH of the filtrate adjusted to 9.4 with 4N NaOH. After stirring for 2 hours at room temperature, the precipitate was filtered off, washed with water, and dried, yielding 2.8 g of crude azithromycin with a purity of 98% after recrystallization.

EXAMPLE 5

To a solution of 8 g (10.9 mmoles) of the imino ether of erythromycin A, prepared by the usual techniques, in 24 ml of acetic acid, there were added 8 g of wet 5% Rh/C (180 g Rh). The mixture was hydrogenated at 70 bar and at room temperature for 2 hours. At the end of this period, 50 ml of an aqueous solution containing 37% formaldehyde (0.67 moles) were added under atmospheric pressure at room temperature, and the mixture was hydrogenated at 40 bar and 40–45° C. for 24 hours. The catalyst was filtered off, and the pH of the filtrate was adjusted to 9.5 with 4N NaOH. After stirring for 2 hours at room temperature, the solids were filtered, washed with water, and dried, yielding 6.1 g of crude azithromycin with a purity of 98% after recrystallization.

EXAMPLE 6

To a solution of 4 g (5.4 mmoles) of the imino ether of erythromycin A, prepared by the usual techniques, in 18 ml of acetic acid and 2 ml of water, there were added 2 g of wet 5% Rh/C (45 mg Rh). The mixture was then hydrogenated at 70 bar and at room temperature for 2 hours. At the end of this period, 35 ml of an aqueous solution containing 37% formaldehyde (0.47 moles) were added under atmospheric pressure at room temperature, and the pH was adjusted between 3 and 4 with 4N NaOH. The mixture was hydrogenated at 40 bar and at a temperature of 40–45° C. for 24 hours. The catalyst was filtered off, and the pH of the filtrate was adjusted to 9.4 with 4N NaOH. After stirring for 2 hours at room temperature, the solid was filtered, washed with water, and dried, yielding 2.7 g of crude azithromycin with a purity of 96% after recrystallization.

EXAMPLE 7

To a solution of 8 g (10.9 mmoles) of the imino ether of erythromycin A, prepared by the usual techniques, in 8 ml of acetic acid and 32 ml of water, there were added 8 g of wet 5% Rh/C (180 mg Rh). The mixture was then hydrogenated at 70 bar and at 40° C. for 2 hours. At the end of this period, 10 g (0.33 moles) of para-formaldehyde was added under atmospheric pressure at room temperature, and the pH of the reaction mixture was adjusted to 4 with NaOH. Hydrogenation was carried out at a pressure of 40 bar and at a temperature of 40–45° C. for 24 hours. The catalyst was filtered off, and the pH of the reaction mixture was adjusted to 9.2 with NaOH 4N. After stirring for 2 hours at room temperature, the solids were filtered, washed with water, and dried, yielding 4.98 g of crude azithromycin with a purity of 97% after recrystallization.

We claim:

1. Process for the preparation of azithromycin from a imino ether precursor thereof, wherein the reduction and the reductive methylation of said imino ether are sequentially carried out without isolation of the product of the reduction and with a noble metal catalyst and hydrogen and, in the reductive methylation, in the presence of formaldehyde or a source thereof.

2. Process of claim 1 wherein the formaldehyde or source thereof is added at the beginning of the reduction phase.

3. Process of claim 1 wherein the formaldehyde or source thereof is added at the beginning of the methylation phase.

4. Process of claim 1, wherein the noble metal is selected from the group consisting of Pd, Pt, Rh and Ru.

5. Process of claim 1, wherein the formaldehyde is formalin or para-formaldehyde.

6. Process of claim 1, wherein the solvent of the reaction mixture comprises acetic acid or formic acid.

7. Process of claim 6, wherein the reaction mixture comprises ethanol.

8. Process of claim 1, wherein the acidity of the reaction medium is controlled through the addition of a buffer salt.

9. Process of claim 8, wherein the buffer comprises sodium acetate.

* * * * *